United States Patent [19]

Sprague, Jr.

[11] Patent Number: 4,799,275

[45] Date of Patent: Jan. 24, 1989

[54] SHOCK-ABSORBING PILLOW

[76] Inventor: William B. Sprague, Jr., 2915 Arbor Dr., West Linn, Oreg. 97068

[21] Appl. No.: 129,292

[22] Filed: Dec. 7, 1987

[51] Int. Cl.$^4$ .............................................. A47G 9/00
[52] U.S. Cl. ........................................... 5/431; 5/434
[58] Field of Search ................. 5/434, 435, 436, 437, 5/468, 481, 450, 461, 431; 297/DIG. 1

[56] References Cited

U.S. PATENT DOCUMENTS 3,066,928  12/1962  Lawrence et al. ........... 297/DIG. 1
4,207,636   6/1980  Ceriani ..................................... 5/434

FOREIGN PATENT DOCUMENTS 1139357  1/1969  United Kingdom .................... 5/434

Primary Examiner—Alexander Grosz

Attorney, Agent, or Firm—Chernoff, Vilhauer, McClung & Stenzel

[57] ABSTRACT

The pillow of the present invention is comprised of a compressible foam core which is wrapped in a membrane that is impervious to air. The membrane has holes defined in it which permit air to flow out of the core when it is compressed and back into the core when it expands after having been compressed. The core is wrapped in a cushion which is made from a softer foam than the core. The cushion provides firmness and permits the pillow to be squeezed without compressing the core. A resilient layer of polyester fiber which surrounds the cushion conforms to the user's body and makes the pillow comfortable to use. The entire structure is held together by ticking made from a nonwoven nonabsorbent fabric or a similar material.

1 Claim, 1 Drawing Sheet

SHOCK-ABSORBING PILLOW

BACKGROUND AND SUMMARY OF THE INVENTION

This invention relates to a pillow which can be used to absorb some of the energy created by deep breathing, coughing, sneezing, or hiccuping and thereby prevent movement of the chest or abdomen in a manner which causes stress at a surgical site located therein, and yet permit the full expansion necessary for the event to occur in its normal manner.

After a patient has undergone thoracic, open heart or abdominal surgery, taking a deep breath, coughing, sneezing or hiccuping can be an extremely painful experience. Yet such events are necessary to help remove fluids from the respiratory system in order to reduce the incidences of respiratory complications following these surgeries.

The pain comes not from the deep breath, cough, or sneeze itself, but from the expansion of the chest or abdominal cavity in a manner which places stress on the surgical site. Thus, if movement of the chest or abdominal cavity can be caused to occur in a way which does not stress the surgical site, sneezing or hiccuping can take place without excessive pain. In the past attempts have been made to achieve this result by clutching a pillow or similar soft compressible object against the surgical site. While clutching conventional pillows may provide some relief, the degree of relief often is limited and varies. This is because a conventional pillow will absorb little shock in this type of situation. If the user clutches the pillow sufficiently close to his or her body to be of any use it often will collapse or become disformed and lose its compressibility. The pillow, then, acts only as a cushion and if any shock is absorbed it will be absorbed by the user's arms. Consequently, the use of a conventional pillow usually either suppresses the cough completely or permits expansion of the chest or abdominal cavity in a manner which places stress on the surgical site. Even if a normal pillow is made stiff enough to provide some shock absorbing capability, after a cough or sneeze has occurred the user will completely compress the pillow as part of the reaction to the cough or sneeze and the pillow will be of no value for subsequent coughs or sneezes when they closely follow the first.

The subject invention overcomes the foregoing problem by providing a pillow having shock absorbing and quick recovery capability. This is accomplished by using a foam core which is encapsulated in a membrane which is impervious to air. A series of holes are placed in the membrane to permit air to pass through it when the core is compressed and again when it expands after having been compressed. By limiting the total area of these holes to a predetermined value, the rate at which air flows through them can be controlled. Thus, the pillow also will compress at a controlled rate, which is slower than would occur with a normal pillow.

The core and membrane are covered with a cushion which is made from a foam material that is softer than the foam used in the core. The cushion provides firmness in the pillow and permits it to be held against the user's chest or abdominal cavity without compressing the core.

The cushion is covered by a polyester retention layer which conforms to the user's body and makes the pillow more comfortable. The retention layer also prevents the cushion from becoming bunched and permits the cover of the pillow to move relative to the cushion.

The outer layer of the pillow is a nonwoven fabric ticking which holds all of the other elements in place. Since the ticking is nonabsorbent it is easy to clean if fluids are spilled on the outer surface.

Accordingly, it is a principal object of the present invention to provide a pillow which has shockabsorbing capability.

It is a further object of the present invention to provide such a pillow wherein the rate at which it can be compressed is limited to a predetermined level.

It is a further object of the present invention to provide such a pillow which limits movement of the chest or abdominal cavity in the region of a surgical site and yet allows full expansion of the remainder of the chest or abdominal cavity.

It is a further object of the present invention to provide such a pillow which is firm and supportive when squeezed against the user's chest or abdominal cavity.

It is a still further object of the present invention to provide such a pillow that conforms comfortably to the user's body.

The foregoing and other objectives, features and advantages of the present invention will be more readily understood upon consideration of the following detailed description of the invention taken in conjunction with the accompanying drawings.

DETAILED DESCRIPTION OF THE INVENTION

Figure 1:
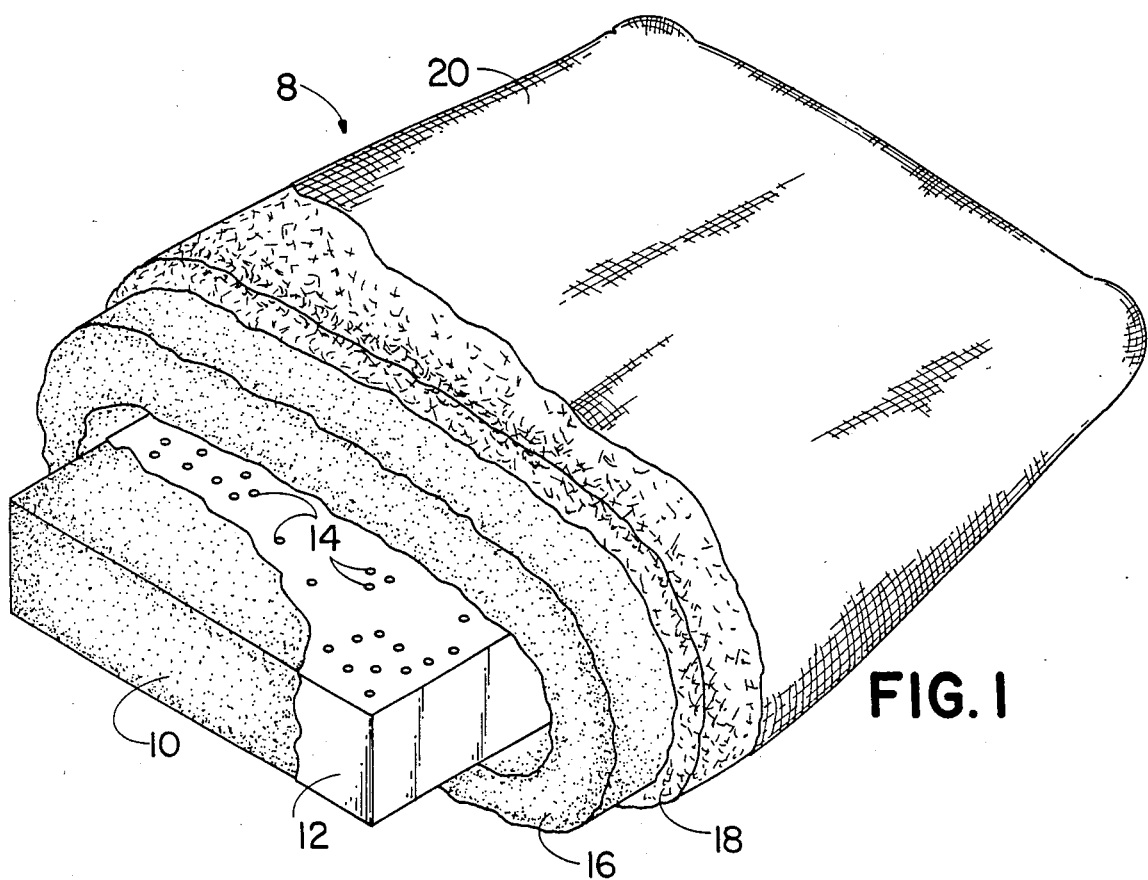
FIG. 1 a fragmentary plan view, partially broken away, of a pillow embodying the features of the present invention.

Referring to FIG. 1 of the drawings, the pillow 8 of the present invention comprises a core 10. The core is resiliently deformable when compressed and returns to its original configuration when released. A relatively low-density open cell foam works well for this purpose. While the desired size of the finished pillow dictates the size of the core, a rectangular block which is $2'' \times 7'' \times 12''$ serves most applications.

The core is encapsulated in a membrane 12 which is impervious to the passage of air. While the membrane can be formed by a number of methods, a relatively simple process is to wrap a thin sheet of flexible polymeric material around the core several times and then fold its ends over and seal them to itself. Openings 14 are located in the membrane to permit air to pass through it when the core is compressed and when it expands after having been compressed. The total area of the holes is limited to a predetermined value in order to control the flow of air through the membrane. Thus, the rate at which the core can be compressed also is controlled. The total hole area normally is set by placing a predetermined number of holes in the membrane. Preferably, the holes are uniformly spaced in the membrane so that air flows into and out of the core uniformly over most of its extent.

Overlying the membrane 12 is a resiliently deformable cushion 16 which is made from a low-density open foam cell which is similar to the material used in the core. However, the foam used in the cushion 16 preferably is less dense than the foam used in the core and, as a result, is easier to compress. The purpose of the cushion is to create a firmness which makes the pillow easy to hold against the chest or abdominal cavity and to create a sense of security that the pillow will perform its intended purpose. The cushion preferably is formed from a 1½ to 2-inch thick sheet of foam whose open sides and ends are glued together to form an enclosed envelope.

The cushion 16 is covered by a thin retention layer 18 which is formed from a polyester fiber material. The retention layer serves to keep the cushion from becoming bunched. In addition, the retention layer conforms to the user's body thereby improving comfort. Finally, the retention layer permits the cover of the pillow to move relative to the cushion.

The final element of the pillow is ticking 20 which serves as a cover to hold the pillow together as an integral unit. The ticking preferably is made from a nonwoven fabric and has sewn seams which permit it to fit snugly around the retention layer, however, other similar materials can be used.

Figure 2:
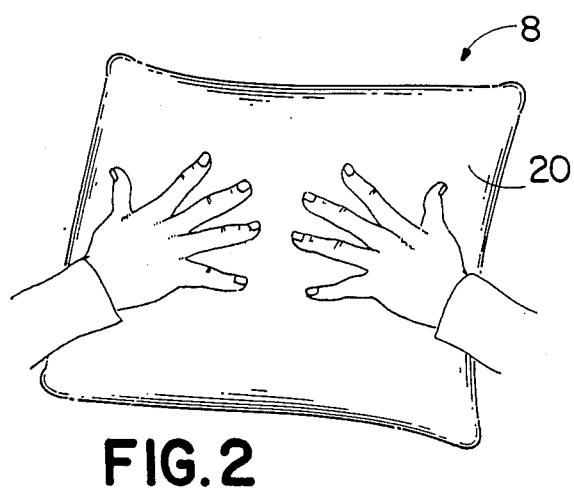
FIG. 2 is a fragmentary plan view of the pillow of FIG. 1 showing how it is used.

The pillow of the present invention is used by holding it tightly against the surgical site, as shown in FIG. 2, when the user needs to cough or take a deep breath or feels that a sneeze or hiccup is about to occur. Since air flow to and from the core 10 is controlled, due to the limited area of the holes 14 in the skin 12, the core acts as a shock absorber to absorb a portion of the energy created by the event. As a result the chest or abdominal cavity is prevented from expanding outwardly at the point of the surgical site, but instead expands in other directions which do not create stress at the surgical site. In addition, because compression of the core is limited it rebounds faster than a normal pillow which permits it to remain effective over a series of coughs or sneezes.

After each cough or sneeze the tendency of the foam to expand causes air to flow back into the core through the openings 14 thereby preparing the core for the next cough. The cushion 16, being more compressible than the core, comforms to the user's body. Thus, even though a portion of the cough or sneeze is absorbed, undue pressure is not felt by the user.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A pillow for permitting unrestricted expansion of a person's chest or abdominal cavity in a manner which does not unduly stress a surgical site located therein when coupling, sneezing or hiccuping, comprising:
   (a) a resiliently deformable central core;
   (b) an impervious membrane which encapsulates said core;
   (c) means defined in said membrane for permitting the flow of air through said membrane at a controlled rate when said core is compressed and again when it expands after having been compressed;
   a resiliently deformable cushion which surrounds said core and said membrane;
   (e) a fiber retention layer which covers said cushion;
   (f) ticking which covers said retention layer; and
   (g) wherein said core and said cushion both comprise open-celled foam with the foam in said cushion being more easily deformed than the foam in said core.

* * * * *

UNITED STATES PATENT AND TRADEMARK OFFICE
CERTIFICATE OF CORRECTION

PATENT NO. : 4,799,275

DATED : January 24, 1989

INVENTOR(S) : William B. Sprague, Jr.

It is certified that error appears in the above-identified patent and that said Letters Patent is hereby corrected as shown below:

Col. 2, line 8      Change "shockabsorbing" to --shock-absorbing--

Col. 4, line 20      Change "coupling" to --coughing--

Col. 4, line 28      Before "a resiliently deformable" indent and insert --(d)--

Signed and Sealed this

Twenty-ninth Day of May, 1990

Attest:

HARRY F. MANBECK, JR.

*Attesting Officer*      *Commissioner of Patents and Trademarks*